United States Patent
McGhin et al.

(10) Patent No.: US 7,983,542 B2
(45) Date of Patent: Jul. 19, 2011

(54) PID COEFFICIENT ADJUSTMENT FOR RESPIRATORY HEATER CLOSED LOOP CONTROL

(75) Inventors: Cary E. McGhin, Sugar Hill, GA (US); Jerry F. Wasinger, Norcross, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 910 days.

(21) Appl. No.: 11/927,013

(22) Filed: Oct. 29, 2007

(65) Prior Publication Data
US 2009/0110379 A1   Apr. 30, 2009

(51) Int. Cl.
*F24H 1/10*   (2006.01)
(52) U.S. Cl. ................................ 392/485; 392/465
(58) Field of Classification Search .................. None
See application file for complete search history.

(56) References Cited

U.S. PATENT DOCUMENTS

| | | | |
|---|---|---|---|
| 4,038,980 A | 8/1977 | Fodor |
| 4,051,205 A | 9/1977 | Grant |
| 4,305,388 A | 12/1981 | Brisson |
| 4,564,748 A | 1/1986 | Gupton |
| 4,621,632 A | 11/1986 | Bartles et al. |
| 4,733,149 A | 3/1988 | Culberson |
| 4,889,280 A | 12/1989 | Grald et al. |
| 5,053,968 A | 10/1991 | Uchinami |
| 5,341,651 A | 8/1994 | Inoue |
| 5,365,922 A | 11/1994 | Raemer |
| 5,368,786 A | 11/1994 | Dinauer et al. |
| 5,558,084 A | 9/1996 | Daniel et al. |
| 5,769,071 A | 6/1998 | Turnbull |
| 5,938,984 A | 8/1999 | Jung |
| 5,943,473 A | 8/1999 | Levine |
| 6,078,730 A | 6/2000 | Huddart et al. |
| 6,082,714 A | 7/2000 | Dornfest et al. |
| 6,258,170 B1 | 7/2001 | Somekh et al. |
| 6,272,933 B1 | 8/2001 | Gradon et al. |
| 6,349,722 B1 | 2/2002 | Gradon et al. |
| 6,455,820 B2 | 9/2002 | Bradenbaugh |
| 6,471,781 B1 | 10/2002 | Tobe et al. |
| 6,584,972 B2 | 7/2003 | McPhee |
| 6,590,366 B1 | 7/2003 | Browning et al. |
| 6,653,605 B2 | 11/2003 | Kneuer |
| 6,694,974 B1 | 2/2004 | George-Gradon et al. |

(Continued)

FOREIGN PATENT DOCUMENTS
EP  1522299 A2  4/2005
(Continued)

OTHER PUBLICATIONS
Manual for Fisher & Paykel Model Nos. MR700, MR720, MR730 Respiratory Humidifiers (Mar. 1998) (48 pages).
(Continued)

*Primary Examiner* — Thor S Campbell
(74) *Attorney, Agent, or Firm* — Wood, Herron & Evans, LLP

(57) ABSTRACT

A heater system is provided for a respiratory system having a PID feedback control in which the coefficients are adjusted, such as in a warm-up process, to correspond to a likely flow rate of gas through a chamber of heated water based on the difference between heat input and heat output in relation to a temperature set point without the need to directly monitor flow rate or humidity level. A steady-state adjustment of the coefficients based on the behavior of the measured temperature in relation to the set point is also disclosed.

26 Claims, 6 Drawing Sheets

U.S. PATENT DOCUMENTS

| | | |
|---|---|---|
| 6,698,186 B2 | 3/2004 | Ueno |
| 6,711,891 B2 | 3/2004 | Kitamura et al. |
| 6,739,337 B2 | 5/2004 | Isaza |
| 6,802,314 B2 | 10/2004 | McPhee |
| 6,813,895 B2 | 11/2004 | Eisenhower et al. |
| 6,918,389 B2 | 7/2005 | Seakins et al. |
| 6,920,388 B2 | 7/2005 | Yasui |
| 6,966,364 B1 | 11/2005 | Babikian et al. |
| 6,988,497 B2 | 1/2006 | Levine |
| 7,051,733 B2 | 5/2006 | Gradon et al. |
| 7,086,399 B2 | 8/2006 | Makinson et al. |
| 2002/0112725 A1 | 8/2002 | Thudor et al. |
| 2002/0129815 A1 | 9/2002 | McPhee |
| 2002/0139367 A1 | 10/2002 | McPhee |
| 2002/0144681 A1 | 10/2002 | Cewers et al. |
| 2003/0154977 A1 | 8/2003 | White et al. |
| 2003/0201684 A1 | 10/2003 | Browning et al. |
| 2003/0209246 A1 | 11/2003 | Schroeder et al. |
| 2004/0060558 A1 | 4/2004 | Gradon et al. |
| 2004/0074493 A1 | 4/2004 | Seakins et al. |
| 2004/0079370 A1 | 4/2004 | Gradon et al. |
| 2004/0149284 A1 | 8/2004 | Smith et al. |
| 2006/0201506 A1 | 9/2006 | Makinson et al. |
| 2008/0028850 A1 | 2/2008 | Payton et al. |
| 2008/0054497 A1 | 3/2008 | Bradley et al. |
| 2008/0054500 A1 | 3/2008 | Bradley et al. |
| 2009/0065002 A1 | 3/2009 | Hunt |

FOREIGN PATENT DOCUMENTS

| | | |
|---|---|---|
| WO | WO03030790 A1 | 4/2003 |

OTHER PUBLICATIONS

Technical Manual Fisher & Paykel Respiratory Humidifier Model Nos. MR700, MR720, MR730, MR 480 (Mar. 2001) (64 pages).

Allegiance Healthcare 510K No. K993833 for Airlife® Heated Ventilator and Anesthesia Breathing Circuits (5 pages) (Dec. 10, 1999).

Operating Manual for Fisher & Paykel Model Nos. MR700, MR720, MR730 Respiratory Humidifiers (Mar. 1994) (46 pages).

Cardinal Health RT110 Data for Circuits, reprinted from the internet Jun. 3, 2006 (2 pages).

Fisher & Paykel Airway Temperature Probes Instructions for Use (3 pages) (2003).

PID COEFFICIENT ADJUSTMENT FOR RESPIRATORY HEATER CLOSED LOOP CONTROL

FIELD OF THE INVENTION

The present invention relates to feedback control for heating of respiratory gas and more particularly to PID closed loop control thereof.

BACKGROUND OF THE INVENTION

Respiratory systems provide breathable gas, such as oxygen, anesthetic gas and/or air directly to a patient's mouth, nose or airway to assist or facilitate breathing by the patient. A ventilator may be used as part of the respiratory system to drive the breathable gas to the patient through an inspiratory limb hose or conduit of a breathing circuit. The breathing circuit may include an expiratory limb hose or conduit to carry expelled air and other gas(es) from the patient back to the ventilator.

It is typically desired to warm and impart humidity to the breathable gas before it is provided to the patient. For that purpose, many respiratory systems include a humidification system having a chamber for holding water and a heater unit to which the chamber may be releasably mounted. The heater unit includes a heater, which may be comprised of one or more heating elements and a metal plate defining a hot plate. A wall of the chamber, such as the bottom surface of the chamber, is thermally conductive and in thermal contact with the hot plate of the heater, to thus heat the water in the chamber. The chamber may be manually refillable, or there may be a water source to selectively fill the chamber as it empties. The breathable gas is coupled to the chamber and is passed through the chamber to be heated and humidified. Examples of heater unit and chamber arrangements are shown in U.S. Pat. Nos. 6,988,497 and 5,943,473. The inspiratory limb carries the heated and humidified gas to the patient and the expiratory limb, if present, carries exhaled air and possibly other gases from the patient. Either or both of the inspiratory and expiratory limbs may be heated such as by heater circuits, which may be comprised of wires running through and along the hose or conduit interior. An example of a breathing circuit with heated limbs is shown in U.S. Pat. No. 6,078,730. In some settings, the limb(s) may not be heated.

In a typical heating arrangement, a temperature set point is established, such as with a thermostat or the like. As the temperature falls below the set point, power to the heater is turned on or increased to bring the temperature back up toward the set point. If the temperature moves above the set point, power to the heater element is reduced or turned off to allow the temperature to drop down toward the set point. In many applications, it is possible to provide more accurate control of the temperature by use of a more sophisticated control based on PID or proportional-integral-derivative control. As is well known, feedback controls operate by obtaining an input signal indicative of the current state of a variable of the system, obtaining a difference or error signal between the input signal and a set point representing the desired value, and outputting a correction signal to be used by the system to drive the system toward the set point. With PID feedback control, the feedback loop involves computations involving empirically or otherwise determined coefficients for each of the proportional, integral and derivative aspects of the error signal.

The coefficients of PID feedback control are typically determined in relation to the nature of the variables which can affect behavior of the system. In the context of a respiratory system, the input value is taken from measured temperatures, and the output is used to regulate power to the heater in an effort to drive the temperature toward the set point. Variables such as flow rate and/or humidity level are generally not monitored or known for purposes of the control, yet they can have an impact on reliable control of the heating element(s) and can affect the temperature and humidity level of the gas reaching the patient. By way of example, the coefficients may be predetermined on the assumption that the flow rate will always be within a certain range. Should the flow rate actually be lower, less heat will be removed from the chamber as the gas flows therethrough than was anticipated and may result in large swings in the resulting temperature, including temperature excursions undesirably above or below the set point. Similarly, if the flow rate is actually higher than the assumed flow rate, more heat will be removed than anticipated, and the control may not be able to get the temperature to the desired set point. The challenge is thus to provide reliable PID feedback control in reliance on temperature measurements in an environment where variations in flow rate and/or humidity level are not known or cannot be directly determined, yet can impact performance of the system.

SUMMARY OF THE INVENTION

The present invention provides for reliable PID feedback control in reliance on temperature measurements in a respiratory system without requiring measurements of flow rate. To that end, and in accordance with the principles of the present invention, the coefficients to be used for the PID feedback control are adjusted based on the difference between heat input and heat output in relation to the set point, particularly when the heater is going through a warm-up process such as from a relatively cold state. Heat input can be obtained by measuring the temperature of the heater and heat output can be obtained by measuring the temperature at the outlet of the chamber. In that regard, it has been determined the temperature differential between the heater and the chamber output in relation to a set point during a warm-up process is indicative of the likely flow rate of the gas through the chamber. The coefficients can then be adjusted to correlate to the likely flow rate and used for normal, or steady-state, operation of the PID feedback control. Yet, there is no need to directly monitor flow rate or humidity level.

The control may initially begin with a set of coefficients correlated to a first flow rate. In a particular embodiment of the invention, bands of flow rates each have a set of PID coefficients associated therewith, and the coefficients are adjusted by selecting the appropriate set of coefficients in relation to the difference in heat input and heat output based on the measured temperature differential between the heater and the chamber output in relation to the set point. In that embodiment, in a warm-up process, the coefficients are initially set to correspond to those for the lowest flow rate band if the warm-up is a start-up of the system, or are set to the coefficients last used if the warm-up is after a pause in operation, for example. After allowing the system to run for a period of time ("the warm-up window"), the temperature differential between the heat input (such as the temperature measured at the heater) and heat output (such as the temperature measured at the chamber output) is obtained (either at that time or based on an average of readings over a segment time during the warm-up window) and compared against a lower boundary and an upper boundary based on the set point temperature. If the temperature differential is at or below the lower boundary, then the coefficients are adjusted to those suitable for a lower flow rate (such as the next lower band of flow rates) for use during steady-state operation of the PID control. If the measured temperature is at or above the upper boundary, the coefficients are adjusted to those suitable for a higher flow rate (such as the next higher band of flow rates) for use during steady-state operation of the PID control.

In one advantageous embodiment, three flow rate bands are utilized, one for lowest flow (such as below 5 lpm), one for highest flow (such as above 10 lpm), and one for intermediate flow (such as 5-10 lpm). In that embodiment, if the temperature differential is at or below the lower boundary the PID coefficients for the lowest flow band are to be used, if at or above the upper boundary the PID coefficients for the highest flow band are to be used, and if between the lower and upper boundaries the PID coefficients for the middle band are to be used. The coefficients are thus adjusted, if necessary, from the set currently being used during the warm-up process to the set for the appropriate flow rate band to be used during steady-state operation.

Adjusting the coefficients during the warm-up process, such as by selection of a set of coefficients based on easily obtained temperature measurements indicative of the difference between heat input and heat output, makes it possible to set the coefficients to be used during steady-state operation based on the likely flow rate of the system, without directly monitoring or obtaining the flow rate or the like. Additionally, adjusting the coefficients during a warm-up process can significantly reduce the time necessary for the heater to achieve the desired temperature.

In some circumstances, it may also be desirable to adjust the coefficients during steady-state operation of the system. While the coefficients could be adjusted from time to time using the same process as utilized during the warm-up process, use of a warm-up process during steady-state operation may not be as advantageous, particularly where the breathing circuit is not heated. To that end, and in accordance with another aspect of the present invention, the coefficients may be adjusted during steady-state operation based on behavior of the measured temperature in relation to the set point. In particular, it has been determined that if the flow rate departs from what was considered likely during the warm-up process, one of two conditions will likely develop. If the actual flow rate is lower than the likely flow rate related to the current set of coefficients, the error between the measured temperature and the set point will display a standard deviation, or rms error, indicative of ringing or temperature excursions above and below the set point. Should the standard deviation exceed an acceptable minimum threshold, the coefficients will be adjusted for a lower likely flow rate. If, on the other hand, the actual flow rate is higher than the likely flow rate related to the current set of coefficients, the error between the measured temperature and the set point will by relatively constant, but will be larger than an acceptable minimum threshold. Should that condition occur, the coefficients will be adjusted for a higher likely flow rate.

Adjusting the coefficients during steady-state operation tracked to errors determined from easily obtained temperature measurements as against the set point temperature, makes it possible to adjust the coefficients during steady-state operation based on changes or offsets in the likely flow rate of the system, again without directly monitoring or obtaining flow rates or the like.

By virtue of the foregoing, there is thus provided reliable PID feedback control in reliance on temperature measurements in a respiratory system without requiring measurements of flow rate. These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTION OF DRAWINGS

Figure 1:
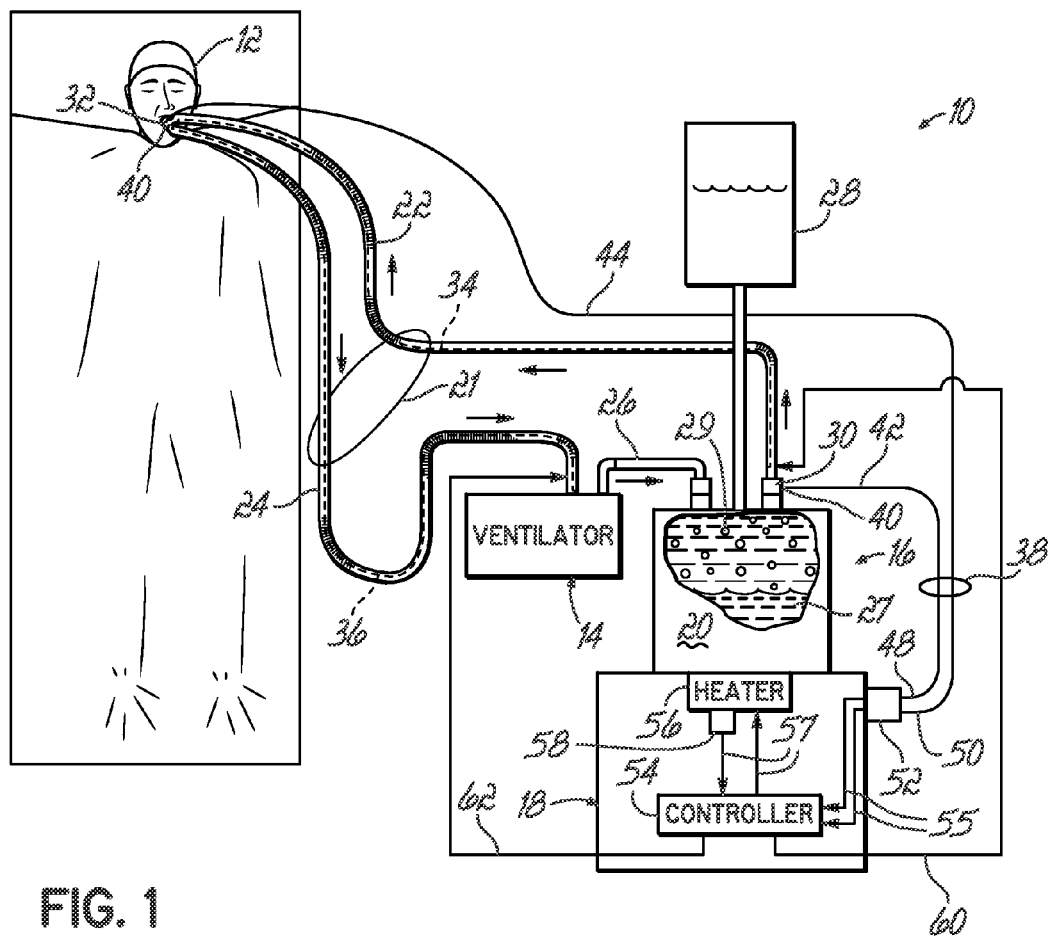
FIG. 1 is a diagram of a respiratory humidifying system embodying principles of the present invention.

FIG. 1 is an exemplary respiratory system 10 for supplying breathable gases to a patient 12. In the illustrated embodiment, the respiratory system 10 includes a ventilator 14, a heater system 16 having a heater unit 18, a heatable container for water such as a disposable chamber 20, and a breathing circuit 21 having a first elongated hose or conduit 22 defining an inspiratory limb 22 and a second elongated hose or conduit 24 defining an expiratory limb 24 (although in some embodiments, breathing circuit 21 may not include an expiratory limb). Ventilator 14 drives breathable gas, such as oxygen, anesthetic gas and/or air, through gas conduit 26 and into an air inlet of chamber 20. Water 27 is received in chamber 20, either by being poured in manually or automatically from a water supply 28 such as a bag or bottle, and which may be vented. Chamber 20 is heated by heater unit 18 to heat up the water 27 therein. Heated water vapor 29 may also be produced within chamber 20 above the level of water 27 therein. The gas from conduit 26 passes over or through the heated water 27 and/or through heated water vapor 29 to become heated and humidified before exiting the chamber 20 as heated and humidified gas. Examples of heater systems are shown in aforementioned U.S. Pat. Nos. 6,988,497 and 5,943,473, and co-pending U.S. patent application Ser. Nos. 11/469,086 filed Aug. 31, 2006 and 11/469,113 filed Aug. 31, 2006, the disclosures of all four of which are incorporated herein by reference in their entireties.

The heated and humidified gas flows from chamber 20 to the patient 12 by passing through inspiratory limb 22. A first end of inspiratory limb 22 is coupled to chamber 20 by a connecting member or joint 30, and a second end of inspiratory limb 22 is coupled to a breathing attachment 32 that facilitates delivery of the gas passed therethrough to the patient 12. The breathing attachment 32 may couple to an invasive apparatus such as an endotrachael tube, or a non-invasive apparatus such as a mask (both not shown) that promotes gas delivery. The gas may be further heated while passing through inspiratory limb 22 to breathing attachment 32 by heater circuit 34 associated with inspiratory limb 22. Expiratory limb 24 allows exhaled air and other gas expelled from patient 12 to pass back to ventilator 14, the atmosphere or elsewhere. Another heater circuit 36 may also be associated with expiratory limb 24 for heating the expelled gas. In the embodiment shown herein, heater circuit 34 and heater circuit 36 may each be comprised of one or more elongated heater wires extending in coiled fashion along and through its associated limb, although other heater circuit configurations may be possible.

Respiratory system 10 may also include a patient temperature cable (PTC) 38 having one or more temperature responsive devices such as thermistor-containing probes as at 40 to provide thermal feedback in the form of temperature readings to heater unit 18 for purposes to be described. Temperature cable 38 includes a first communication cable 42 and a second communication cable 44. One of the temperature probes 40 is coupled to joint 30 at the entry to inspiratory limb 22 to provide a temperature reading via first communication cable 42 indicative of the actual measured temperature of the heated and humidified gas exiting from chamber 20 ("the output temperature"). The output temperature can be seen as a heat output of chamber 20 and may be used as a heat output value. Another of probes 40 is coupled to breathing attachment 32 such as at the exit of inspiratory limb 22 to provide a temperature reading via second communication cable 44 indicative of the actual measured temperature of the humidified gas being provided to the patient ("the patient temperature"). First communication cable 42 has an end 48 electrically coupled to heater unit 18 to communicate the output temperature to heater unit 18. Similarly, second communication cable 44 has an end 50 electrically coupled to heater unit 18 to communicate the patient temperature to heater unit 18. Ends 48 and 50 may be advantageously secured together through a connector 52 to facilitate coupling the first and second cables 42, 44 to a mating socket (not shown) on heater unit 18. Further details of a suitable cable 38 and probes 40 are set out in concurrently-filed U.S. patent application Ser. No. 11/927,020 and concurrently-filed U.S. patent application Ser. No. 11/927,077, the disclosures of both of which are incorporated herein in their entirety by reference.

The output temperature and the patient temperature readings are coupled to a controller 54 of heater unit 18 as at 55. Controller 54 is operatively associated with a heater 56 as at 57. A temperature sensitive device such as a thermistor 58 (FIG. 2) thermally coupled to heater 56 provides readings of the actual measured temperature of heater 56 to controller 54 ("the input temperature"). The input temperature is representative of the heat input to the chamber 20, and may be used as a heat input value. An example of one suitable heater 56 is described in concurrently-filed U.S. patent application Ser. No. 11/926,982 the disclosure of which is incorporated herein by reference in its entirety. Controller 54 utilizes the input temperature as will be explained hereinafter to regulate power to heater 56 so as to attempt to maintain a temperature of the water 27 in chamber 20 at a desired temperature in relation to an established set point in order to desirably heat and humidify the breathable gas(es) passing through chamber 20. Controller 54 may also be operatively associated with heater circuits 34, 36 as at 60, 62 and may also be adapted for independent selective energization of heater circuits 34, 36.

Figure 2:
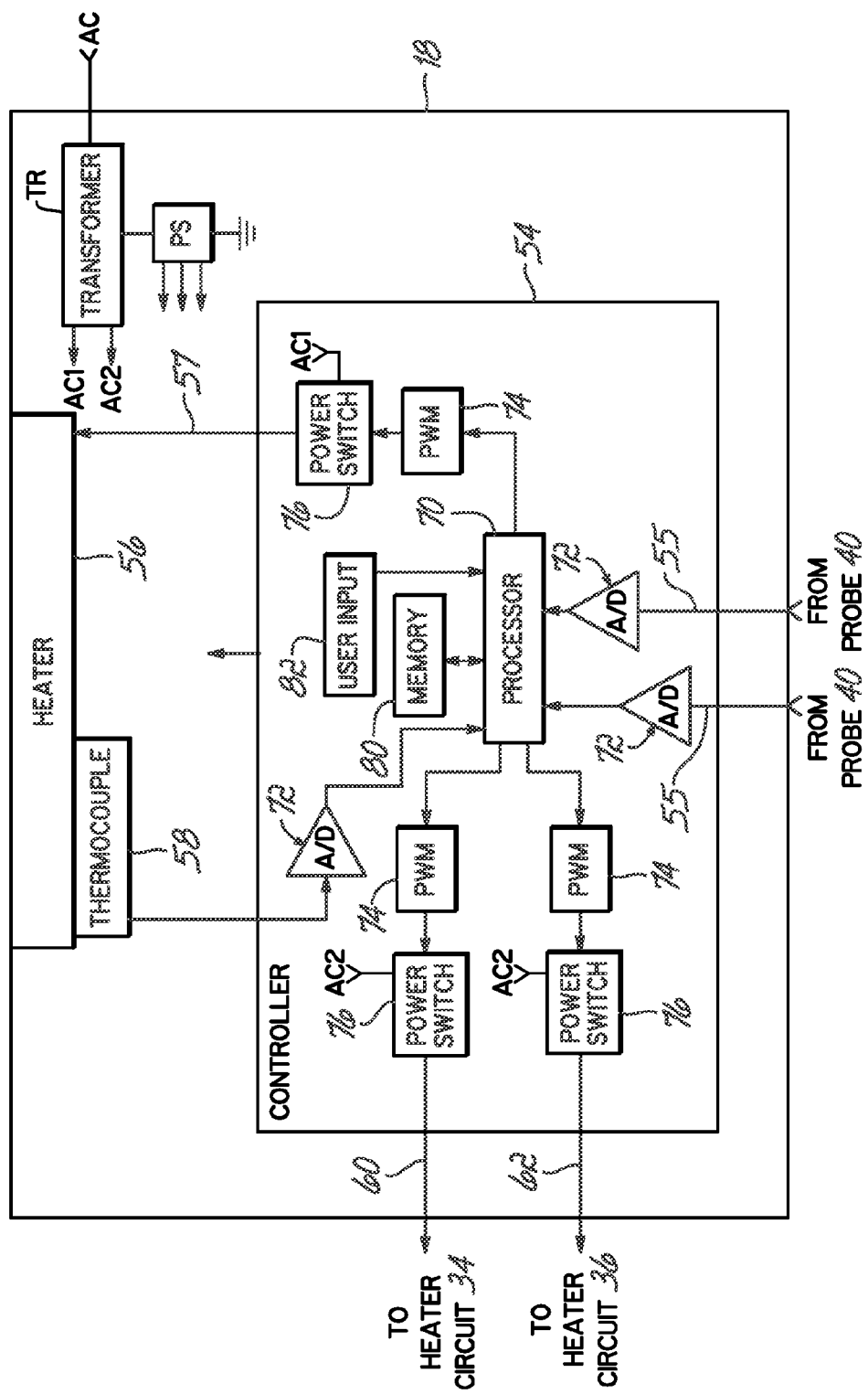
FIG. 2 is a schematic diagram of the heater unit of FIG. 1.

As seen in greater detail in FIG. 2, controller 54 includes a processor 70, which may be a microprocessor or other computer or programmable logic device. Processor 70 receives the input temperature readings through an A/D converter 72 from temperature responsive device 58 coupled to heater 56, and outputs signals via a control circuit 74, such as a pulse width modulator ("PWM"), to drive a power switch 76, such as a triac, to selectively energize heater 56 so as to regulate the temperature thereof. Output temperature readings and patient temperature readings from respective probes 40 may also be coupled to processor 70 via respective A/D converters 72. Similarly, signals from processor 70 may be coupled via respective further control circuits 74 and further power switches 76 to selectively energize heater circuits 34 and 36, if such heater circuits are present and to be utilized. Controller 54 also includes a memory 80 to store the operating programs or algorithms and control data used by processor 70 as well as input data, such as the set point temperature, obtained from a user (not shown) through an input dial or keyboard as at 82. As will be appreciated, while the various devices are shown as being independently coupled to processor 70, they may communicate over one or more common busses.

Figure 3:
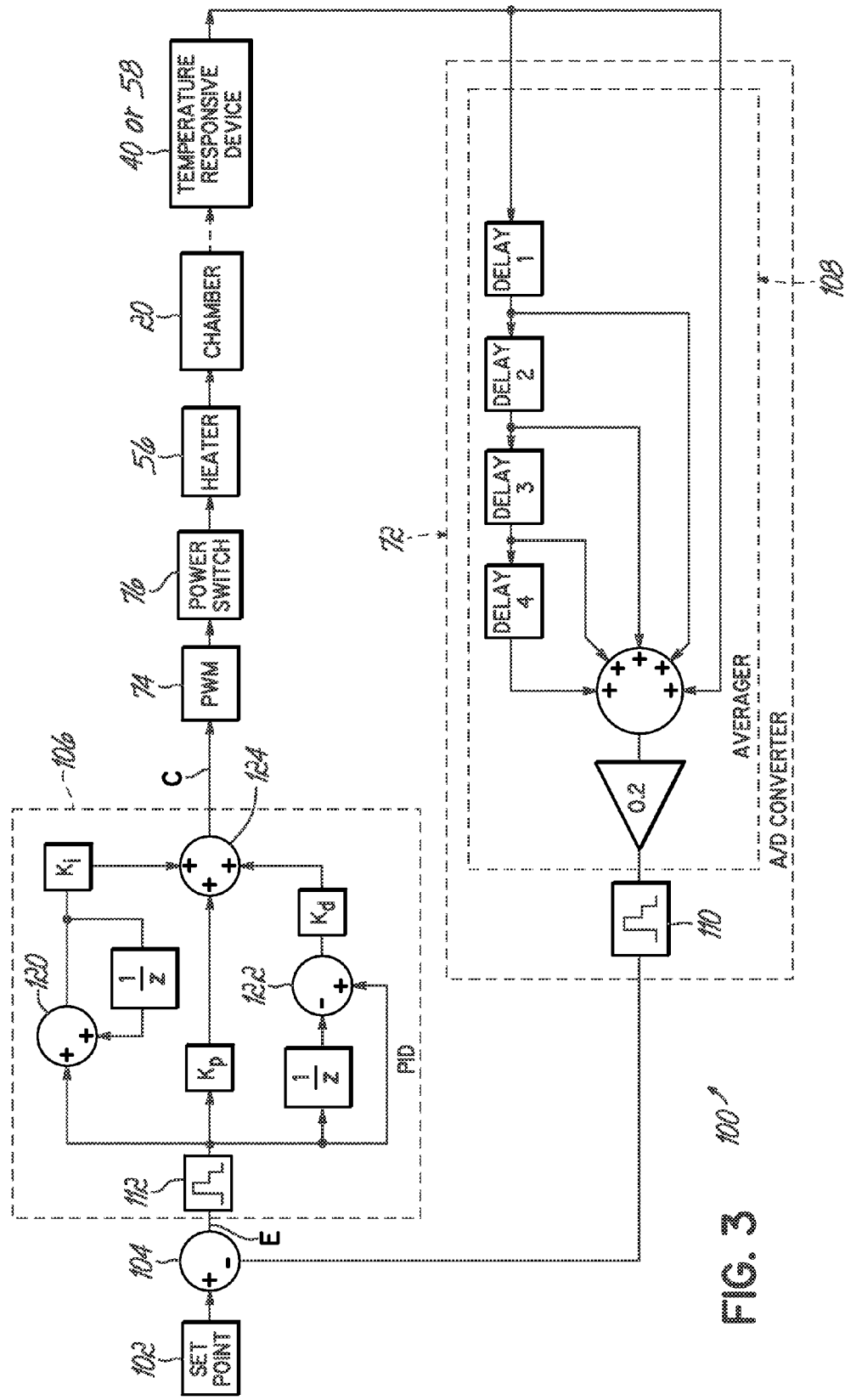
FIG. 3 is a diagram of a PID feedback control implemented in the controller of the heater unit of FIG. 2 for purposes of explaining the principles of the present invention.

Advantageously, processor 70 implements a PID feedback control 100 as shown diagrammatically in FIG. 3. To that end, PID feedback control 100 is in the form of a feedback loop adapted to compare a set point temperature $T_{sp}$ as at 102, which may be stored in memory 80, with the appropriate temperature reading from the applicable temperature responsive device (such as one of probes 40 or thermistor 58) as obtained from applicable A/D converter 72. The comparison is accomplished in a summing block 104 to produce an error or difference signal E (such as in degrees Celsius) representing the departure of the measured temperature from the applicable set point temperature. Error signal E is coupled through the PID feedback algorithm 106 which produces a correction signal C (such as in watts) which is used to drive control circuit 74 to modulate power switch 76 either by turning it on and off or by varying its conductance as desired whereby to selectively energize heater 56 in a manner intended to desirably heat and humidify gas passing through chamber 20.

Control circuit 74, switch 76, behavior of chamber 20 and water 27 therein, and temperature responsive device 58 all interject time delays which are taken into account by A/D converter 72 by averaging the readings from temperature responsive device 58 over several intervals, for example five, with an averaging circuit or algorithm 108 and digitized with a zero-order hold circuit or algorithm 110 to provide the output to summing element 104. Algorithm 106 is developed in the z-transfer domain and includes a zero-order delay circuit or algorithm 112 of error signal E which is then processed to produce the correction signal C through a combination of a scaled amount of a proportion of the error signal E, a scaled amount of the integral of the error signal E, and a scaled amount the derivative of the error signal E as is generally understood by those familiar with feedback controls. The scaling for each aspect is based on a corresponding coefficient, with the coefficient for the proportional aspect being referred to as $K_p$, the coefficient for the integral aspect being referred to as $K_i$, and the coefficient for the derivative aspect being referred to as $K_d$.

The proportional aspect is obtained by multiplying the output from zero-order hold 112 of error signal E by $K_p$. The integral aspect is obtained by adding the output of zero-order hold 112 of current error signal E with a value of the previous output from summing block 104 delayed by, for example 1/100th second. The accumulated value from summing circuit or algorithm 120 is multiplied by $K_i$ to produce the integral term of the PID algorithm. The derivative aspect is obtained by obtaining the difference between the output of zero-order hold 112 for E at time t and the delayed value of E as determined in subtracting circuit or algorithm 122, and multiplying that result by $K_d$. The three aspects are then logically summed as at summing circuit or algorithm 124 to produce correction signal C. The following is a representative formula of the foregoing:

$$C = K_p E(t) + K_d (dE(t)/dt) + K_i \int E(t) dt$$

One area of concern is the coefficients used in the PID feedback algorithm 106. While the PID feedback control 100 will normally provide desired and advantageous temperature control, the flow rate of the gas through chamber 20 can impact the reliability of that control and can thus affect the temperature and humidity level of the gas reaching the patient 12. The flow rate of gas through chamber 20 can vary from 1 or 2 liter per minute (lpm) to between 50 and 100 lpm, usually within 2 lpm to 70 lpm. As gas flows through chamber 20, thermal energy is removed from water 27 roughly in proportion to the gas flow rate. To raise the temperature of water 27 to the desired level, heater 56 must supply enough heat to compensate for that taken by the gas flowing through chamber 20. Thus, at low air flow rates, less heat is required to heat the water, while at high flow rates, a much greater amount of heat is necessary to raise the temperature of the water. Another variable that is dependent on flow rate is the thermal time constant of the water. At high flow rates, the system will change temperature much faster than when the flow rate is low.

The flow rate of the gas is generally not available to controller 54, so it would have been thought to establish and program into memory 80 a fixed, single set of coefficients based on the typical flow rate expected for system 10. But the set of coefficients programmed into memory 80 could turn out to be based upon a flow rate that is too high or too low relative to the actual flow rate. By way of example, if the coefficients are selected on the assumption that the flow rate will always be within a certain range, should the flow rate actually be lower, less heat will be removed from chamber 20 as the gas flows therethrough than was anticipated. The result may be large swings in the resulting temperature, including temperature excursions undesirably above or below the set point. Similarly, if the flow rate is actually higher than the assumed flow rate, more heat will be removed than anticipated, and the control 100 may not be able to get the temperature to the desired set point. The challenge is thus to provide reliable PID feedback control in reliance on temperature measurements in an environment where variations in flow rate and/or humidity level are not known or cannot be directly determined, yet can impact performance of the system.

In accordance with the principles of the present invention, the coefficients are adjusted in relation to the difference between heat input and heat output, particularly when the heater 56 is going through a warm-up process such as from a relatively cold state. One warm-up algorithm or process 200 used to select the coefficients for steady-state operation will be described with reference to FIG. 4. With the system 10 running with a pre-selected set of coefficients, at step 202, heat input may be determined by obtaining a reading of the input temperature from temperature responsive device 58 and heat output may be determined by obtaining a reading of the output temperature from probe 40 coupled to the outlet of chamber 20, both as obtained from the applicable, respective A/D converter 72. While shown as one step, step 202 could actually be made up of multiple steps. At step 204, a heat differential is determined, such as the difference between the input temperature and the output temperature ($T_d$). The heat differential $T_d$ is compared in step 206 to the set point temperature $T_{sp}$ to provide an indication whether the coefficients currently being utilized in control 100 are properly correlated to the likely flow rate of the gas through chamber 20. In that regard, if the differential $T_d$ departs from an expected relationship with the set point temperature $T_{sp}$ then the flow rate is likely not sufficiently close to the flow rate of the current coefficients, and they must be adjusted to the likely flow rate. To that end, if $T_d$ is too small in relation to $T_{sp}$, it is likely that the flow rate is lower than expected, so the coefficients are to be adjusted for a lower flow rate at step 208. Similarly, if $T_d$ is too large in relation to $T_{sp}$, it is likely that the flow rate is higher than expected, so the coefficients are to be adjusted for a higher flow rate at step 210. If the relationship between $T_d$ and $T_{sp}$ is acceptable, then no change is made at step 212.

Figure 5:
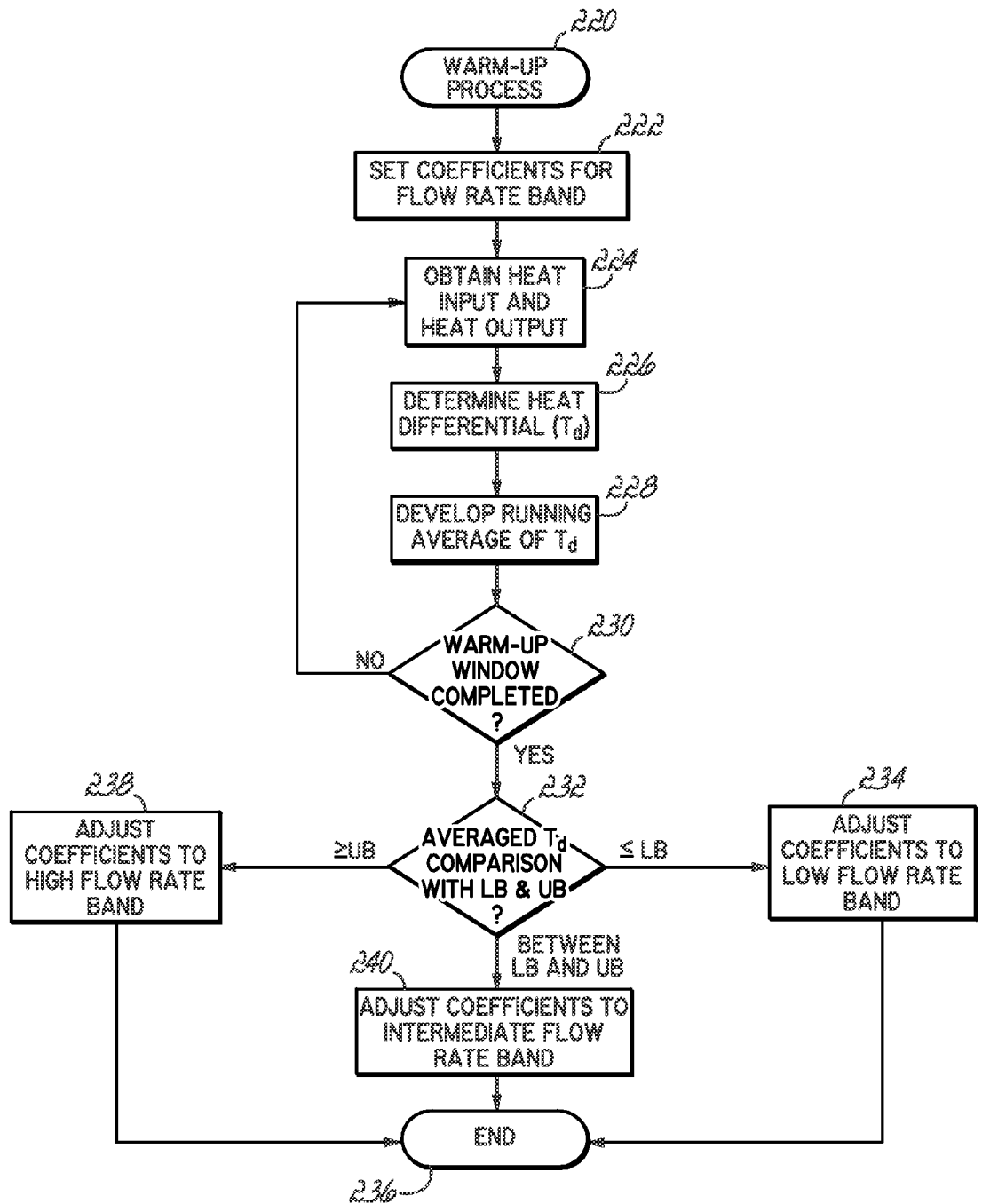
FIG. 5 is a flow chart of another warm-up process for adjusting coefficients to be used by the PID feedback control of FIG. 3 in accordance with the principles of the present invention.

As will be described in connection with another warm-up process 220 shown in FIG. 5, $T_d$ may advantageously be obtained after a sufficient period of time ("warm-up window") for the heater 56 to likely have overcome various outside influences other than flow rate, and may further advantageously be obtained from a comparison of average input temperatures and output temperatures over a selected segment of time in that warm-up window. For purposes of the process of FIG. 5, three sets of coefficients have been predetermined and stored in memory 80, such as in a table or the like. Each set corresponds to a selected band of flow rates, such as a first set for low flow rates (such as below 5 lpm), a second set for high flow rates (such as above 10 lpm), and at third set for intermediate flow rates (such as from 5 lpm to 10 lpm). Also, lower and upper boundaries (LB and UB, respectively) are established in fixed relation to the temperature set point $T_{sp}$, and the process of FIG. 5 is undertaken to adjust the coefficients based on the relationship of $T_d$ to the boundaries LB and UB.

The boundaries and sets of coefficients are determined empirically for the particular arrangement and components of system 10 employed so as to obtain desired performance thereof. To that end, the coefficients for one embodiment with a heated breathing circuit 21 are determined to be:

| Flow Rate Band | $K_p$ | $K_i$ | $K_d$ |
|---|---|---|---|
| Less than 5 lpm | 25 | 0.001 | 1000 |
| From 5 lpm to 10 lpm | 100 | 0.001 | 500 |
| Greater than 10 lpm | 250 | 0.0025 | 250 |

The coefficients for one embodiment where the breathing circuit is not heated are determined to be:

| Flow Rate Band | $K_p$ | $K_i$ | $K_d$ |
|---|---|---|---|
| Less than 5 lpm | 15 | 0.01 | 3000 |
| From 5 lpm to 10 lpm | 25 | 0.015 | 3000 |
| Greater than 10 lpm | 75 | 0.025 | 3000 |

Controller 54 can be adapted to determine whether a heated breathing circuit 21 is being used as described in concurrently filed U.S. patent application Ser. No. 11/927,004 the disclosure of which is incorporated herein by reference in its entirety. Alternatively, a user input (not shown) is provided to controller 54 to indicate whether breathing circuit 21 is heated.

The boundaries LB and UB are correlated to the set point $T_{sp}$ according to the following:

$$UB = 2.0399 T_{sp} - 36.3292$$

$$LB = 1.2675 T_{sp} - 21.1213$$

Returning to FIG. 5, at step 222, a set of coefficients is selected for a particular flow rate band for initial operation of system 10 during the warm-up process 220. If the system 10 is first being turned on, such that heater 56 is expected to be cold, the coefficients for the low flow rate band may be selected at step 222. If the system 10 had been running, and was paused, the warm-up process 220 will start again if breathing circuit 21 includes a heated inspiratory limb 22, or will start again if inspiratory limb 22 is not heated but the patient temperature at probe 40 is less than 30° C. If inspiratory limb 22 is not heated and the patient temperature at probe 40 is at or above 30° C., the coefficients for the flow rate band last being used before the pause are continued and the process bypassed to its end (step 236). If system 10 is not paused, at step 224, with the system 10 running, heat input may be determined by obtaining a reading of the input temperature from temperature responsive device 58 and heat output may be determined by obtaining a reading of the output temperature from probe 40 coupled to the outlet of chamber 20, both as obtained from the applicable, respective A/D converter 72. While shown as one step, step 224 could actually be two steps. At step 226, a heat differential is determined, such as the difference between the input temperature and the output temperature ($T_d$). The heat differential $T_d$ is accumulated and averaged, such as over a one-minute sliding segment of time, at step 228.

At step 230, a determination is made whether the end of the warm-up window has been reached, which in the embodiment shown herein, has been established at ten minutes, or 600 seconds. If the end of the warm up window has not been reached, the process loops back to step 224. The loop between steps 224 and 230 occurs about every one second, such that ten readings are taken in 10-second sliding segments. If, however, the end of the warm-up window has been reached at step 230, the process continues to step 232 whereat the averaged heat differential is compared to LB and UB which thus results in comparison of the heat differential $T_d$ against the temperature set point $T_{sp}$. In that regard, if, at step 232, the averaged heat differential is at or below LB, then the coefficients are adjusted to (which may include being retained at) the coefficients for the low flow rate band at step 234, and the warm up process ends as at 236 and steady-state operation will then ensue with the adjusted coefficients. If, however, at step 232, the averaged heat differential is at or greater than UB, the coefficients are adjusted to (which may include being retained at) the coefficients for the high flow rate at step 238 and the process ends and steady-state operation will then ensue with the adjusted coefficients. Further, if at step 232, the averaged heat differential is between LB and UB the coefficients are adjusted to (which may include being retained at) the coefficients for the intermediate flow rate band at step 240, and the process ends and steady-state operation will then ensue with the adjusted coefficients. To adjust coefficients, the appropriate set may be obtained from the table of memory 80 and loaded into a portion of memory 80 used during operation of processor 70. It will also be appreciated the flow rate bands could be selected as low if the differential is less than LB, high if the differential is above UB, and intermediate if the differential is between or equal to either of LB and UB.

Figure 4:
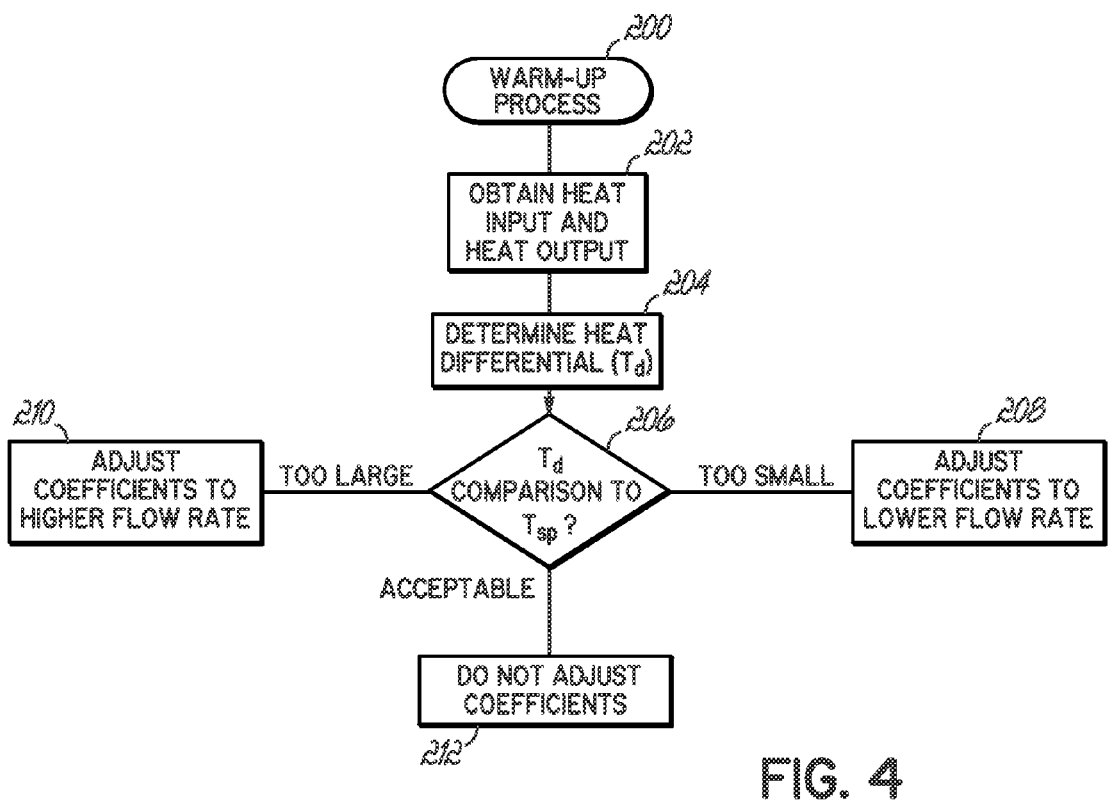
FIG. 4 is a flow chart of one warm-up process for adjusting coefficients to be used by the PID feedback control of FIG. 3 in accordance with the principles of the present invention.

In use, system 10 is turned on, and a set of coefficients, such as the low flow set, is utilized to begin heating heater 56. The warm-up process of FIG. 4 or FIG. 5 is undertaken in order to adjust the coefficients of the PID feedback control for the likely flow rate being encountered by system 10. Thereafter, steady-state operation will ensue utilizing the coefficients as adjusted during the warm-up process. If the steady-state operation is interrupted, such as by a pause in operation of system 10, the warm-up process may again be undertaken to adjust the coefficients before proceeding to steady-state operation, or may be bypassed, as explained above.

Adjusting the coefficients during the warm-up process, such as by selection of a set of coefficients based on easily obtained temperature measurements indicative of the relationship between the set point and the difference between heat input and heat output, makes it possible to set the coefficients to be used during steady-state operation based on the likely flow rate of the system, without directly monitoring or obtaining the flow rate or the like. Additionally, adjusting the coefficients during a warm-up process can significantly reduce the time necessary for the heater to achieve the desired temperature.

Figure 6:
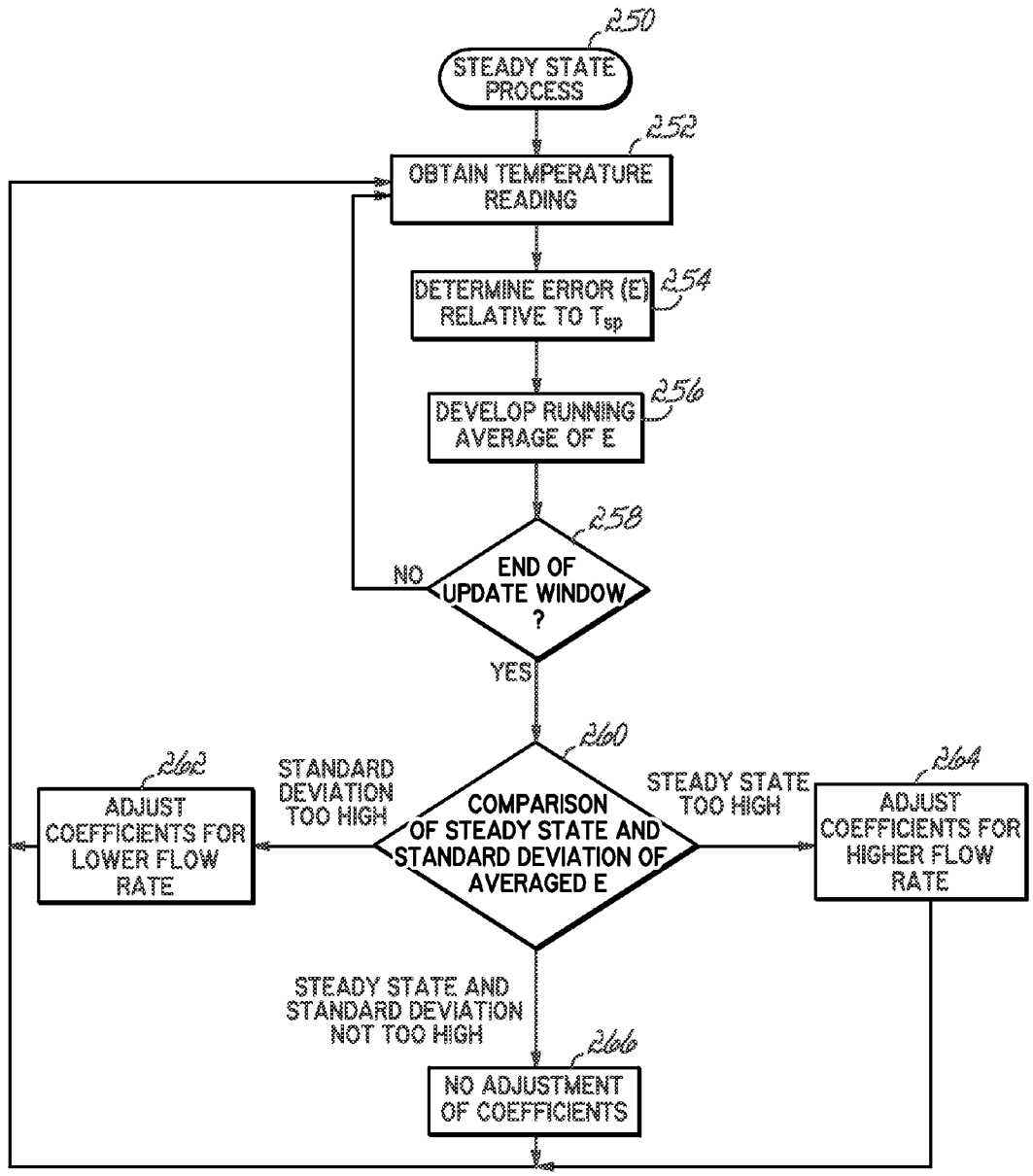
FIG. 6 is a flow chart of a steady-state process for adjusting coefficients of the PID feedback control of FIG. 3 in accordance with the principles of the present invention.

While not critical, it may be advantageous to also adjust the coefficients during steady-state operation with a focus on the relationship of the measured temperature related to the set point temperature rather than heat differential between the input and output temperatures. To that end, and with reference to FIG. 6, a steady-state process 250 is described in which the coefficients may be adjusted during steady-state operation based on behavior of the measured temperature (either the patient temperature where breathing circuit 21 is not heated or the output temperature where the breathing circuit is heated) in relation to the set point (being set to the patient temperature where breathing circuit 21 is not heated or set to the output temperature where the breathing circuit is heated).

At step 252, a temperature reading is obtained taken from the appropriate probe 40. At step 254, an error signal E is determined reflecting the difference between the measured temperature and the set point expected for that temperature. In the steady-state process 250, adjustment of the coefficients need not be undertaken very often, and so at step 256, the error signals are accumulated and averaged, such as over a five-minute sliding segment of time. At step 258, a determination is made whether the end of an update window has been reached, which in the embodiment shown herein is established at thirty minutes. If the end of the update window has not been reached, the process loops back to step 252. The loop between steps 252 and 258 occurs about every ten seconds, such that thirty readings are taken every five minute segment. If, however, the end of the update window has been reached at step 258, the process continues to step 260 whereat the averaged error signals are evaluated for both a steady-state difference and a standard deviation or rms error.

In particular, process 250 can be used to determine whether the flow rate has departed from what was considered likely during the warm-up process (or a pre-determined set of coefficients if a warm-up process is not undertaken) based on the expectation that, under such circumstances, one of two conditions will likely develop. If the actual flow rate is lower than the likely flow rate related to the current set of coefficients, the error between the measured temperature and the set point will display a standard deviation, or rms error, indicative of ringing or temperature excursions above and below the set point. Should the standard deviation at step 260 be determined to exceed an acceptable minimum threshold, such as 0.5° C. by way of example, then the coefficients will be adjusted for a lower likely flow rate, such as by selecting the coefficients for the next lower flow rate band at step 262, and the process may loop back to step 252 to be repeated.

If, on the other hand, the actual flow rate is higher than the likely flow rate related to the current set of coefficients, the error between the measured temperature and the set point will by relatively constant, but will be below the set point. Should that condition occur, the steady-state error will be determined at step 260 to exceed a minimum threshold, such as −1° C. by way of example, and the coefficients will be adjusted for a higher likely flow rate such as by selecting the coefficients for the next higher flow rate band at step 264 before looping back to step 252. If neither condition is present, i.e., both standard deviation and steady-state error are not too high, then no adjustment of the coefficients is necessary and at step 266 the process may loop back to step 252.

In use, during steady-state operation of system 10, the temperature may be measured and the error from the applicable set point evaluated for steady-state error and standard deviation. If either exceeds a respective minimum threshold, then the coefficients are adjusted. Adjusting the coefficients during steady-state operation tracked to errors determined from easily obtained temperature measurements as against the set point temperature, makes it possible to adjust the coefficients during steady-state operation based on changes in the likely flow rate of the system, again without directly monitoring or obtaining flow rates or the like.

Heater unit 18 may also include a power supply (PS) to provide one or more regulated DC voltage levels for use in powering the various aspects of controller 54. Heater 56 may be powered with AC power directly or through a tap AC1 of a transformer (TR), and heater circuits 34, 36 may be powered through power supply PS or through taps from the transformer (TR), with the various power switches 76 regulating operation thereof as described. Heater unit 18 may also include one or more displays, input controls such as buttons and dials or the like, and alarm indicators (all not shown), and may further have various interface inputs and outputs such as to couple to a source of AC power (not shown) and to the heater circuits 34, 36 and PTC cable 38. Controller 54 may also include various control and power management functions. Further, heater unit 18 may be mounted with a self-aligning lock mount (also not shown). Various of the foregoing are shown in concurrently-filed U.S. patent application Ser. No. 11/927,000; U.S. patent application Ser. No. 11,927,038; U.S. patent application Ser. No. 11,927,044; U.S. patent application Ser. No. 11,927,054; and U.S. patent application Ser. No. 11/927,068; the disclosures of all five of which are incorporated herein by reference in their entireties.

By virtue of the foregoing, there is thus provided reliable PID feedback control in reliance on temperature measurements in a respiratory system without requiring measurements of flow rate.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, adjustments to the coefficients may involve changes to all, or fewer than all of them. Also, while one advantageous embodiment only has one set (namely the third set) of coefficients for an intermediate flow rate band, more or other flow rate bands could be employed with respective sets of coefficients. Additionally, while ventilator 14 is shown as driving the gas through chamber 20, it will be appreciated that other gas systems could be employed, such as from a hospital oxygen supply, a CPAP or BiPAP pump, or other air or oxygen pumping system. Further, when present, the heater circuits 34, 36 may each be controlled by a PID feedback control like that of FIG. 3, with the measured temperature coming from the applicable probe 40 and the correction signal C driving the applicable control circuit 74 and switch 76 for the respective heater circuit 34 or 36. However, it may not be necessary to adjust the coefficients of that or those PID feedback control(s), such that the coefficients may be fixed. In one embodiment, the coefficients for the PID feedback controls of the heater circuits 34 and 36 are determined to be $K_p=200$; $K_i=0.025$; and $K_d=1000$. Heater circuits 34, 36 may be independently controlled in order to reduce rainout in limbs 22 and/or 24 as described in U.S. patent application Ser. No. 11/926,990 the disclosure of which is incorporated herein by reference in its entirety. Additionally, while not shown, the various temperatures may be monitored and system 10 shut down and/or an alarm set off if the temperature reading exceeds a maximum level. The invention in its broader aspects is therefore not limited to the specific details, representative apparatus and methods and illustrative examples shown and described. Accordingly, departures may be made from such details without departing from the scope or spirit of Applicants' general inventive concept.

Having described the invention, what is claimed is:

1. A method of controlling the heating of a breathable gas to be supplied to a patient in which a PID feedback control having a set of coefficients is used comprising:
heating water in a chamber;
passing the breathable gas through the chamber to heat the breathable gas; and
adjusting the coefficients based on a heat differential between the heat input to the water and the heat output from the chamber in relation to a temperature set point.

2. The method of claim 1 further comprising obtaining a heat input value and a heat output value and determine the differential therebetween.

3. The method of claim 2, wherein obtaining a heat input value includes obtaining a temperature reading of a heater adapted to heat the water in the chamber, obtaining a heat output value includes obtaining a temperature reading of the heated breathable gas, and determining the differential includes computing a difference in the obtained temperature readings.

4. The method of claim 3, wherein the coefficients are adjusted to correspond to a lower flow rate if the difference is too small in relation to the set point and to correspond to a higher flow rate if the difference is too large in relation to the set point.

5. The method of claim 1, wherein the coefficients are adjusted to correspond to a lower flow rate if the relationship involves the heat differential being too small in relation to the set point and to correspond to a higher flow rate if the relationship involves the heat differential being too large in relation to the set point.

6. The method of claim 1 further comprising comparing the heat differential to upper and lower boundaries related to the set point and adjusting the coefficients to a lower flow rate if the heat differential is below the lower boundary and to a higher flow rate if the heat differential is above the upper boundary.

7. The method of claim 1 further comprising comparing the heat differential to upper and lower boundaries related to the set point and adjusting the coefficients to a lower flow rate if the heat differential is at or below the lower boundary and to a higher flow rate if the heat differential is at or above the upper boundary.

8. A method of controlling the heating of a breathable gas to be supplied to a patient in which a PID feedback control having a set of coefficients is used comprising:
heating water in a chamber;
passing the breathable gas through the chamber to heat the breathable gas; and
adjusting the coefficients based on a heat differential between the heat input to the water and the heat output from the chamber in relation to a temperature set point, wherein there are a plurality of sets of coefficients each corresponding to a respective band of flow rates, a first set of coefficients corresponding to a low flow rate band, a second set of coefficients corresponding to a high flow rate band, and at least a third set of coefficients corresponding to an intermediate flow rate band between the low and high flow rate bands, the method further comprising initially operating with a set of coefficients and wherein adjusting the coefficients includes selecting one of the sets of coefficients.

9. The method of claim 8 wherein lower and upper boundaries are established in relation to the set point, the first set of coefficients being selected if the heat differential is below the lower boundary, the second set of coefficients being selected if the heat differential is above the upper boundary, and the third set of coefficients being selected if the heat differential is between the upper and lower boundaries.

10. The method of claim 9, the first set of coefficients being selected if the heat differential is at or below the lower boundary.

11. The method of claim 10, the second set of coefficients being selected if the heat differential is at or above the upper boundary.

12. The method of claim 9, the second set of coefficients being selected if the heat differential is at or above the upper boundary.

13. The method of claim 8 wherein initial operation occurs with the first set of coefficients.

14. The method of claim 8 wherein obtaining a heat input value includes obtaining a temperature reading of a heater adapted to heat the water in the chamber, obtaining a heat output value includes obtaining a temperature reading of the heated breathable gas, and determining a difference includes computing a difference in the obtained temperature readings, wherein the difference is used to select the set of coefficients.

15. The method of claim 8 wherein the set point correlates to a desired temperature of the breathable gas as it exits from the chamber.

16. The method of claim 8 further comprising readjusting the coefficients by selecting one of the sets of coefficients in relation to an error signal between a set point temperature and an actual measured temperature.

17. The method of claim 16 wherein the set of coefficients for a next lower flow rate band is selected if a standard deviation of the error signal exceeds a minimum threshold.

18. The method of claim 16 wherein the set of coefficients for a next higher flow rate band is selected if a steady-state of the error signal exceeds a minimum threshold.

19. The method of claim 1 wherein the set point correlates to a desired temperature of the breathable gas exiting from the chamber.

20. The method of claim 1 further comprising readjusting the coefficients in relation to an error signal between a set point temperature and an actual measured temperature.

21. The method of claim 20 wherein the coefficients are readjusted for a higher flow rate if a standard deviation of the error signal exceeds a minimum threshold.

22. The method of claim 20 wherein the coefficients are readjusted for a lower flow rate if a steady-state of the error signal exceeds a minimum threshold.

23. A method of controlling the heating of a breathable gas to be supplied to a patient in which a PID feedback control having a set of coefficients is used comprising:
   heating water in a chamber;
   passing the breathable gas through the chamber to heat the breathable gas; and
   adjusting the coefficients in relation to an error signal between a set point temperature and an actual measured temperature, wherein the coefficients are adjusted for a lower flow rate if a standard deviation of the error signal exceeds a minimum threshold.

24. A method of controlling the heating of a breathable gas to be supplied to a patient in which a PID feedback control having a set of coefficients is used comprising:
   heating water in a chamber;
   passing the breathable gas through the chamber to heat the breathable gas; and
   adjusting the coefficients in relation to an error signal between a set point temperature and an actual measured temperature, wherein the coefficients are adjusted for a higher flow rate if a steady-state of the error signal exceeds a minimum threshold.

25. The method of claim 23, wherein the set point temperature corresponds to a desired temperature of the breathable gas as it exits from the chamber, the method further comprising obtaining the actual measured temperature by measuring the temperature of the breathable gas as it exits from the chamber.

26. The method of claim 24, wherein the set point temperature corresponds to a desired temperature of the breathable gas as it exits from the chamber, the method further comprising obtaining the actual measured temperature by measuring the temperature of the breathable gas as it exits from the chamber.

* * * * *